(12) United States Patent
Enck

(10) Patent No.: US 11,511,279 B2
(45) Date of Patent: Nov. 29, 2022

(54) AUTOMATIC CORRECTION OF TUBE LABEL INFORMATION

(71) Applicant: Roche Diagnostics Operations, Inc., Indianapolis, IN (US)

(72) Inventor: Robert Enck, Winnenden (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 300 days.

(21) Appl. No.: 16/672,869

(22) Filed: Nov. 4, 2019

(65) Prior Publication Data

US 2020/0156075 A1 May 21, 2020

(30) Foreign Application Priority Data

Nov. 16, 2018 (EP) .................................. 18206773

(51) Int. Cl.
*B01L 3/00* (2006.01)
*G01N 35/00* (2006.01)
(Continued)

(52) U.S. Cl.
CPC ...... *B01L 3/5453* (2013.01); *G01N 35/00732* (2013.01); *G01N 35/04* (2013.01);
(Continued)

(58) Field of Classification Search
CPC .............. B01L 3/5453; G01N 35/00732; G01N 35/04; G01N 2035/00752;
(Continued)

(56) References Cited

U.S. PATENT DOCUMENTS 10,527,635 B1 * 1/2020 Bhatia ............. G01N 35/00871
2011/0045521 A1 2/2011 Itoh
(Continued)

FOREIGN PATENT DOCUMENTS

| JP | 2002-040034 A | 2/2002 |
| WO | 2015/049298 A1 | 4/2015 |
| WO | 2015/056649 A1 | 4/2015 |

OTHER PUBLICATIONS

European Search Report dated May 14, 2019, in Application No. EP 18206773.6, 2 pp.

*Primary Examiner* — Jill A Warden
*Assistant Examiner* — John McGuirk
(74) *Attorney, Agent, or Firm* — Roche Diagnostics Operations, Inc.

(57) ABSTRACT

A method to handle tubes in a diagnostic laboratory automation system comprising a control device and a tube-analyzing device is presented. The tube-analyzing device comprises a tube identification reader, a tube type recognition unit, a sample color determination unit, and a tube consistence unit. The tube identification reader reads tube identification device. The tube type recognition unit identifies tube type. The sample color determination unit determines sample color. The tube consistence unit determines sample consistency. The sample tube type, the tube type, the sample color, the sample consistency are send to the control device. The control device determines a construed tube type from one or more of the information of the tube type, the sample color, and the sample consistency. The control device checks whether the tube type matches the construed tube type and changes a used tube type from the tube type to the construed tube type.

10 Claims, 2 Drawing Sheets

(51) Int. Cl.
*G01N 35/04* (2006.01)
*G01N 35/10* (2006.01)

(52) U.S. Cl.
CPC .............. *G01N 2035/00752* (2013.01); *G01N 2035/0493* (2013.01); *G01N 2035/1025* (2013.01); *G01N 2201/102* (2013.01)

(58) Field of Classification Search
CPC ... G01N 2035/0493; G01N 2035/1025; G01N 2201/102; G01N 35/00613; G01N 33/491; G01N 21/25; G01N 21/00; G06K 17/0022
See application file for complete search history.

(56) References Cited

U.S. PATENT DOCUMENTS

| | | |
|---|---|---|
| 2016/0018427 A1 | 1/2016 | Streibl et al. |
| 2016/0025756 A1* | 1/2016 | Pollack ................ G01N 35/026 436/47 |
| 2016/0266157 A1 | 9/2016 | Suzuki et al. |
| 2017/0185815 A1 | 6/2017 | Itoh |

* cited by examiner

AUTOMATIC CORRECTION OF TUBE LABEL INFORMATION

CROSS-REFERENCE TO RELATED APPLICATIONS

This application claims priority to EP 18206773.6, filed Nov. 16, 2018, which is hereby incorporated by reference.

BACKGROUND

The present disclosure generally relates to a method to identify sample tubes in a diagnostic laboratory and to a diagnostic laboratory system, which identifies sample tubes.

Diagnostics laboratories are highly automated today. Typically, a variety of tubes with different biological samples are processed to get relevant medical parameters.

Usually, in a first step, some kind of tube identification is attached to the tube. The tube identification such as, for example, a RFID-tag, printed bar code or similar, can be read by a tube identification reader, as is known in the art. Based on the identification on the tube, the different stations of the automated diagnostic lab can perform the respective task for the specific tube. For instance, in a pre-analytic step, some tubes can be centrifuged while others are sorted to specific racks that are collecting samples to be analyzed in a specific analyzer.

In addition, in the pre-analytic phase, the tube can be decapped, if necessary, and aliquots can be taken and placed into secondary tubes. For these actions, the tube type and the liquid level of the sample are also detected.

Therefore, there is a need for to provide for an efficient and reliable processing of sample tubes.

SUMMARY

According to the present disclosure, a system and a method for handing sample tubes in a diagnostic laboratory automation system comprising a control device and a tube analyzing device. The tube analyzing device can comprise a tube identification reader, a tube type recognition unit, a sample color determination unit, and a tube consistence unit. The method can comprise reading a tube identification of a sample tube by the tube identification reader to determine sample tube type, identifying tube type by the tube type recognition device, determining sample color of a sample in the sample tube by the sample color determination unit, determining sample consistency of the sample in the sample tube by the tube consistence unit, sending the sample tube type, the tube type, the sample color, and the sample consistency to the control device, determining a construed sample tube type by the control device construed by one or more of the information of: the tube type, the sample color, and the consistency of the sample in the tube, checking by the control device whether the sample tube type matches the construed sample tube type and, in the case of a mismatch, changing a used sample tube type from the sample tube type to the construed sample tube type, and handling the sample tube by the diagnostic laboratory automation system according to the used sample tube type.

Accordingly, it is a feature of the embodiments of the present disclosure to provide for an efficient and reliable processing of sample tubes. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
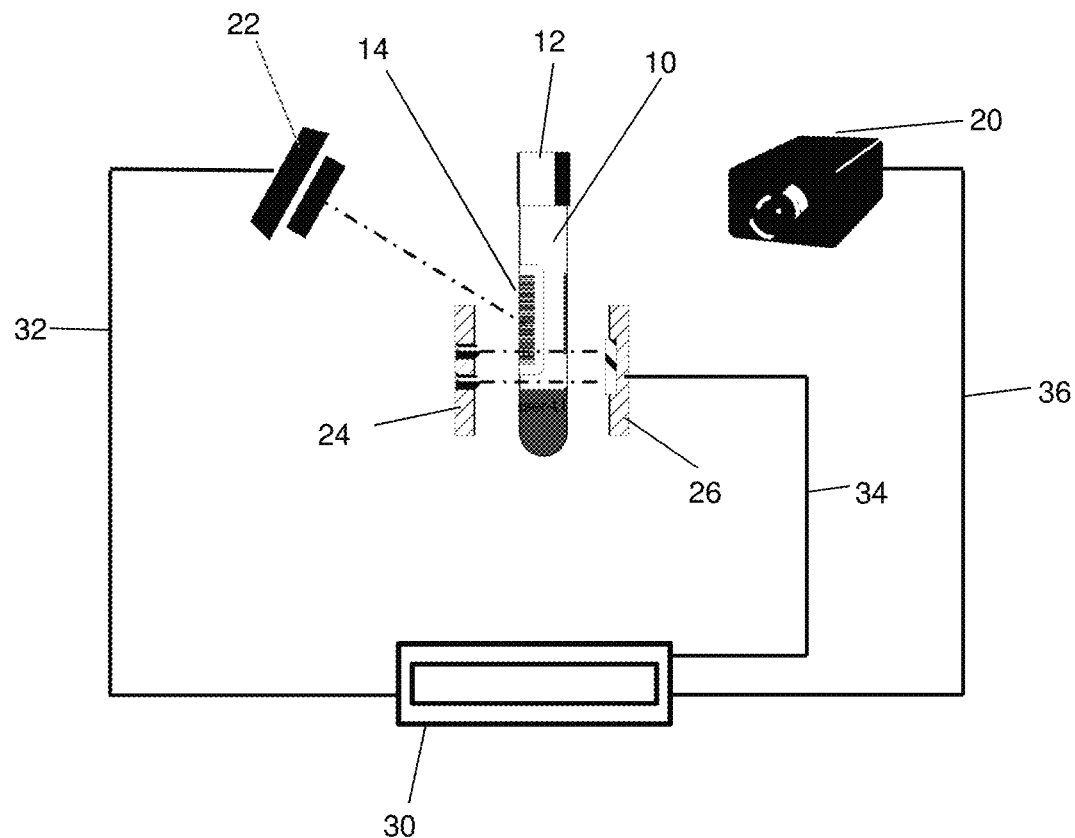
FIG. 1 illustrates a schematic view of parts of a diagnostic laboratory automation system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for handling sample tubes in a diagnostic laboratory automation system comprising a control device and a tube-analyzing device is presented. The tube-analyzing device can comprise a tube identification reader, a tube type recognition unit, a sample color determination unit, and a tube consistence unit.

The tube identification reader can read a tube identification of a sample tube to determine the sample tube type. For instance, a bar code can be attached to the tube and can determine whether the sample in the tube is blood, urine, saliva, serum, or any other biological sample. Other attached identifiers, or marks, or transmitters like RFID on or in the tube are also possible. Furthermore, the sample tube type can be classified as centrifuged or not centrifuged. Another further classification can be lipaemic, hemolytic, or icteric. For full blood, a sub classification can be mixed, sedimented, centrifuged or with gel centrifuged. A sample tube type can be, for example, urine, lipaemic or full blood, sedimented, or saliva, icteric or serum, icteric and so on.

The tube type recognition device can identify the type of tube. Usually in a laboratory, different kind of tubes with different height, diameter, form, material, and cap can be used.

The sample color determination unit determines the color of the sample in the sample tube.

The tube consistence unit can determine the consistency of the sample in the tube. Here consistency can mean a degree of firmness, density, viscosity, or resistance to movement or separation of constituent particles.

The determined sample tube type, the tube type, the color of the sample and the consistency of the sample can be sent to the control device via a respective data connection system.

The data connection system can comprise respective receivers and transmitters and signal propagation methods for the devices.

The control device can determine a construed sample tube type construed from at least one, more, or all of the information of the type of tube, the color of the sample, and the consistency of the sample in the tube.

The control device can check whether the sample tube type matches the construed sample tube type and, in the case of a mismatch, can change a used sample tube type from the sample tube type to the construed sample tube type.

The diagnostic laboratory automation system can handle the tube according to the used sample tube type.

In one embodiment, the control device can determine a confidence level of the construed sample tube type from one or more of the information of the type of tube, the color of the sample, and the consistency of the sample in the tube, and can only change the used sample tube type from the sample tube type to the construed sample tube type if the confidence level is above or equal a predetermined confidence level.

In one embodiment, one or more of its cap geometry, its cap color, and its tube geometry can determine the tube type.

In one embodiment, the tube type recognition device can be a camera and a control unit of the camera can determine the cap geometry and cap color by image processing methods.

In one embodiment, the tube consistence unit can be a laser liquid level detection unit determining the consistency of the tube by scanning the tube.

In one embodiment, the tube identification reader can be a barcode reader reading a barcode attached to the tube.

In one embodiment, a diagnostics laboratory automation system characterized by means adapted to perform the method according to one of the preceding claims.

A diagnostic laboratory automation system comprising a control device and a tube-analyzing device is also disclosed. The tube-analyzing device can comprise a tube identification reader, a tube type recognition unit, a sample color determination unit, and a tube consistence unit. The tube identification reader is configured to read a tube identification of a sample tube to determine the sample tube type. The tube type recognition device is configured to identify the type of tube. The sample color determination unit is configured to determine the color of the sample in the sample tube. The tube consistence unit is configured to determine the consistency of the sample in the tube. The control device is configured to receive the sample tube type, the tube type, the color of the sample, and the consistency of the sample. The control device is configured to determine a construed sample tube type construed from one or more of the information of the type of tube, the color of the sample, and the consistency of the sample in the tube. The control device is configured to check whether the sample tube type matches the construed sample tube type and to change a used sample tube type from the sample tube type to the construed sample tube type.

In one embodiment, the tube identification unit can be part of a pre-analytic device.

In one embodiment, the diagnostics laboratory automation system can comprise a central automation logic unit configured to run a laboratory IT system. The control device can be comprised in the central automation logic unit.

Referring initially to FIG. 1, FIG. 1 shows a schematic view of parts of a diagnostic laboratory automation system. A tube 10 can usually be transported by a transport device through a pre-analytic system or device. The tube 10 usually can comprise a cap 12 when it enters the diagnostic laboratory. In the embodiment shown in FIG. 1, the tube 10 can comprise a bar code 14 attached to the outer surface of the tube. Other forms of identification such as, for example, 2D bar code or wireless identification tags such as RFID chips can also be used.

The bar code can be read by a bar code reader 22 to identify the sample tube type. The sample tube type related to the bar code can be transmitted to a control device 30.

In a next station or place in the pre-analytic system, the tube can be examined with a laser liquid level detection system (LLLD) 24, 26. The LLLD system can comprise a light emitting part 24 and a light detecting part 26. The tube can be scanned with laser light and the detected part of the light which passes through the tube can be dependent on the content of the tube. Such a system is, for example, described in WO 2015/049298 herewith incorporated by reference.

With a LLLD system 24, 26, the consistency of the tube can be determined, i.e., whether there exists several separated phases in the content of tube which usually differs by different densities which can be separated by a centrifuge device. The information of the consistency of the tube can also be send to the control device 30. For instance, in a blood sample, usually two layers exist: in the bottom of the tube a blood clot and above the serum sometimes separated by a separation gel, depending on the kind of tube used.

In a further station or part of the pre-analytic system, images of the tube 10 can be made with a camera system 20. With image processing methods, the camera system 20 can be calibrated and the tube images can be used to identify the geometry of the tube and, if applicable, of the tube cap as well as the color of the cap and the color of the sample inside the tube.

Image processing methods can be used to identify or classify the tube depending on the color of the cap and the geometry of tube and cap. Furthermore, the color of the sample can be used to automatically identify or classify the type of sample.

The image processing methods can be realized either in the camera system 20 or at the control device 30, which can receive all the information obtained of the tube. Other devices capable of image processing at any appropriate place in the laboratory or via wireless connection to any kind of data processing system locally or in a cloud application can be possible, too.

The schematic view of FIG. 1 is simplified in such that it looks like that the bar code-reader 22, the camera 20, and the LLLD 24, 26 are inspecting the tube at the same point in space in the diagnostic laboratory automation system. This is usually not the case and these devices can be installed at different areas in the laboratory or in the pre-analytic system with the respective environment to support the respective functionality e.g., by shielding the used laser beams, provide a background for better imaging and the like. Nevertheless, the operations are usually centralized in a pre-analytic instrument or in an entry area of tubes of the laboratory to guarantee a meaningful sequential and coherent processing of the tubes in the lab.

Figure 2:
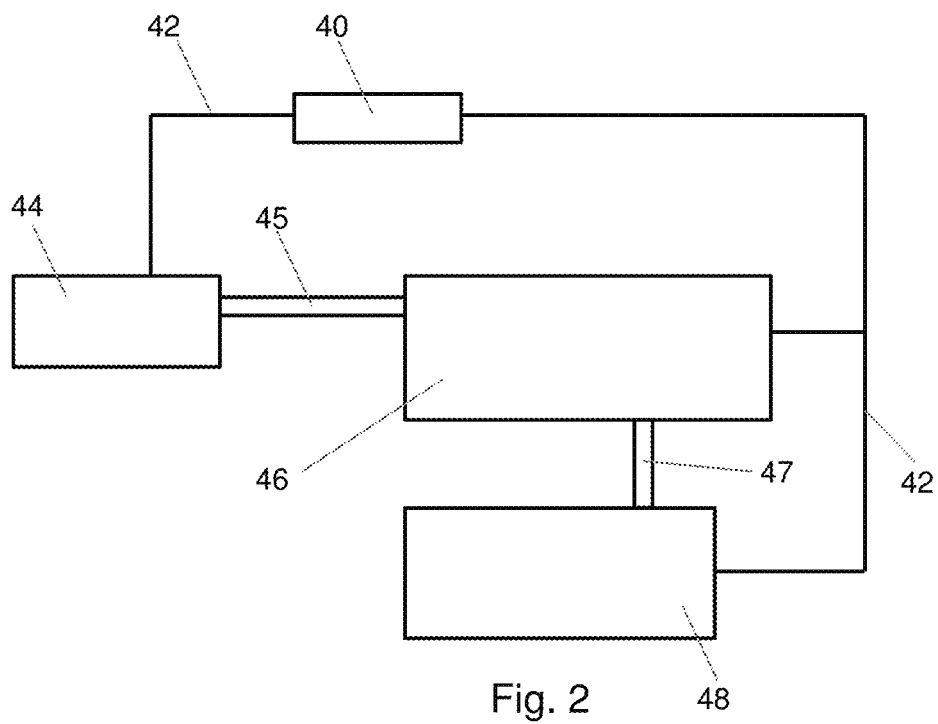
FIG. 2 illustrates a block diagram of a simplified diagnostic laboratory automation system according to an embodiment of the present disclosure.

FIG. 2 shows a schematic block diagram of a diagnostic laboratory automation system. A pre-analytic device 44 can receive the sample tubes. These can be identified, classified, decapped, and aliquot into secondary tubes and may be recapped and the sample tube and/or its aliquots can be put on a transport device 45. The transport device 45 can transport the tubes to an analyzer 46 to analyze the sample in the tubes. Afterwards, the tubes can be transported to a post analytic system 48 by a transport device 47. In the post-analytic device 48, the tubes can be stored in controlled environmental conditions and, if necessary, resend to the analyzer 46 or any other not shown analyzer or thrown away in the appropriate way.

A lab control unit 40 can be connected to any device via a lab bus 42 to control the required way and analysis of the samples in the tubes. If the lab control unit 40 receives the data of the pre-analytic system 44 as described above with reference to FIG. 1, the lab control unit 40 can adjust the correct sample tube type to directly send the tubes to the necessary analyzer 46 or, at least, to order at the analyzer 46, the necessary and appropriate analysis.

Figure 3:
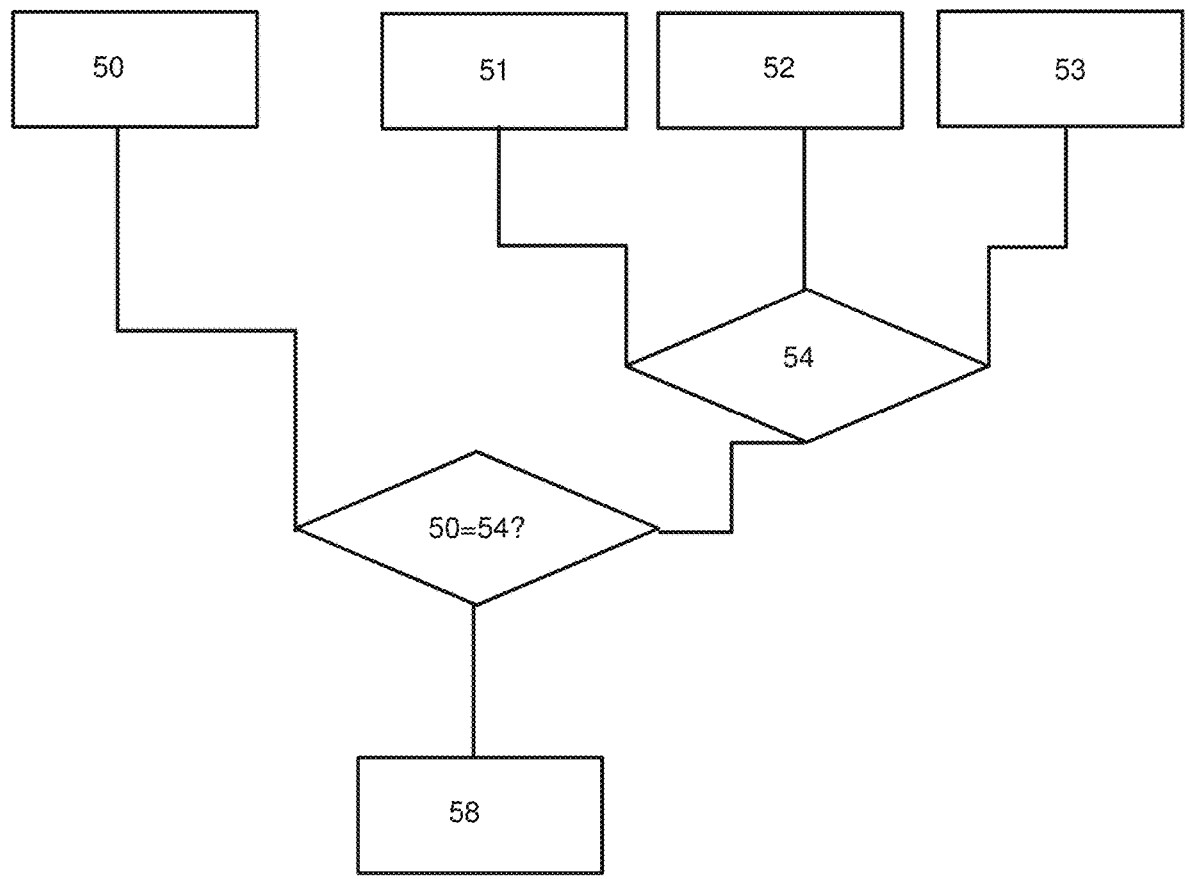
FIG. 3 illustrates a block diagram of a method to handle sample tubes according to an embodiment of the present disclosure.

FIG. 3 is a block diagram of the method to handle sample tubes in the diagnostic laboratory. The tube identification reader can identify the sample tube type 50. The tube type recognition device can identify the type of tube 51. The sample color determination unit can determine the color of the sample 52. The tube type recognition device and the sample color determination unit can both be realized in the embodiment shown in FIG. 1 by one device: the camera system 20. This does not need to be always the case. The tube consistence unit can determine the consistency of the sample 53.

From the type of the tube 51, the color of the sample 52 and the consistency of the sample 53, the method can determine a construed sample tube type 54. A decision table can realize this.

For instance, if the type of tube 51 is related to a type of tube used for urine, the color of the sample is yellow, and the consistency of the sample is uniform, then the construed sample tube type can be urine.

In another case, if the type of tube is related to a kind used for blood samples, the color is yellow due to a lipaemic sample, and the consistency identifies three distinguished layers, the construed sample tube type can be centrifuged blood.

Therefore, the construed sample tube type can classify in this example into urine, non-centrifuged blood and centrifuged blood.

The following table summarizes the classifications which may be possible:

| Sample type\class | Type of tube | Color of sample | Consistency |
|---|---|---|---|
| Urine | urine | yellow, clear | one phase |
| Urine, hemolytic | urine | light red | one phase |
| Urine lipaemic | urine | white-yellow, opaque | one phase |
| Blood with separation gel | blood | red and white clear | two phases |
| Full blood | blood | red | one phase |
| Blood sedimented | blood | clear and dark red | two phases |
| Blood with gel centrifuged | blood | dark red and white and clear | three phases |

Further classification can be implemented depending on the kind of biological liquids used in the laboratory. For example, the last class in the table can be separated in serum icteric, serum hemolytic and serum lipaemic.

It can also be possible to consider measurement errors or overlapping classification classes in the classes. In addition, it can happen that a sample is in the "wrong" or not expected tube. Than the color of the sample and the consistency would contradict the type of tube classification. In these cases, the determination of the construed sample tube type can have a confidence level, e.g., of ⅔ if two of three classes identifies the sample type. This can be used to only rely on the determination only if a given confidence level is reached by the classification.

If the confidence level cannot be reached, an error message can be generated and the respective tube can be send to an error handling area in the laboratory automation system.

The color identification can be realized by color values determined from the camera, which can be calibrated for a specific color space. This can allow to better distinguish between the different sample types In a further step of the method, the construed sample tube type 54 can be compared with the sample tube type 50. If they match, the sample tube type 50 can be used as the final result 58 to decide on the further processing of the sample.

If the construed sample tube type 54 and the sample tube type are different, then the construed sample tube type 54 can be used as the final result 58 of the method to decide on further processing of the sample.

If the construed sample tube type 54 cannot be determined due to inconsistencies in the type of tube 50, the color of the sample 52 and the consistency of the sample 53, the sample can be send to an error output station in the laboratory for further investigations on the sample tube.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method to handle sample tubes in a diagnostic laboratory automation system comprising a control device and a tube analyzing device wherein the tube analyzing device comprises a tube identification reader, a tube type recognition unit, a sample color determination unit, and a tube consistence unit, the method comprising:
   reading a tube identification of a sample tube by the tube identification reader to determine sample type in the sample tube, wherein the sample type is one of: urine, hemolytic urine, lipaemic urine, blood with separation gel, full blood, sedimented blood, or centrifuged blood with separation gel;
   identifying tube type by the tube type recognition device;
   determining sample color of a sample in the sample tube by the sample color determination unit;
   determining sample consistency of the sample in the sample tube by the tube consistence unit;
   sending the sample type, the tube type, the sample color, and the sample consistency to the control device,
   determining a construed sample type and a confidence level of the construed sample type by the control device from the tube type, the sample color, and the consistency of the sample in the tube, wherein the construed sample type is one of: urine, hemolytic urine, lipaemic urine, blood with separation gel, full blood, sedimented blood, or centrifuged blood with separation gel;
   checking by the control device whether the sample type matches the construed sample type and, in the case of a mismatch, changing a used sample type from the sample type to the construed sample type only if the confidence level is above or equal to a predetermined confidence level; and handling the sample tube by the diagnostic laboratory automation system according to the used sample type.

2. The method according to claim 1, wherein one or more of the following determine the tube type: its cap geometry, its cap color, and/or its tube geometry.

3. The method according to claim 2, wherein the tube type recognition device is a camera.

4. The method according to claim 3, wherein a control unit of the camera determines the cap geometry and cap color by image processing.

5. The method according to claim 1, wherein the tube consistence unit is a laser liquid level detection unit that determines the consistency of the sample by scanning the sample tube.

6. The method according to claim 1, wherein the tube identification reader is a barcode reader that reads a barcode attached to the sample tube.

7. A diagnostics laboratory automation system configured to perform the method according to claim 1.

8. A diagnostic laboratory automation system, the diagnostic laboratory automation system comprising:
a control device; and
a tube-analyzing device, wherein the tube-analyzing device comprises,
a tube identification reader, wherein the tube identification reader is configured to read a tube identification of a sample tube to determine a sample type in the sample tube wherein the sample type is one of: urine, hemolytic urine, lipaemic urine, blood with separation gel, full blood, sedimented blood, or centrifuged blood with separation gel,
a tube type recognition unit, wherein the tube type recognition device is configured to identify the type of tube,
a sample color determination unit, wherein the sample color determination unit is configured to determine the sample color of the sample in the sample tube, and
a tube consistence unit, wherein the tube consistence unit is configured to determine the consistency of the sample in the tube;
wherein the control device is configured to receive the sample type, the tube type, the color of the sample, the consistency of the sample, wherein the control device is configured to determine a construed sample type and a confidence level of the construed sample type from the type of tube, the color of the sample, and the consistency of the sample in the tube, wherein the construed sample type is one of: urine, hemolytic urine, lipaemic urine, blood with separation gel, full blood, sedimented blood, or centrifuged blood with separation gel, and wherein the control device is configured to check whether the sample type matches the construed sample type and to change a used sample type from the sample type to the construed sample type in the case of a mismatch only if the confidence level is above or equal to a predetermined confidence level.

9. The diagnostic laboratory automation system according to claim 8, wherein the tube identification reader is part of a pre-analytic device.

10. The diagnostic laboratory automation system according to claim 8, further comprising,
a central automation logic unit configured to run a laboratory IT system, wherein the control device is located in the central automation logic unit.

* * * * *